United States Patent [19]
Smith

[11] Patent Number: 5,454,785
[45] Date of Patent: Oct. 3, 1995

[54] METHOD OF WITHDRAWING AND EXCHANGING CATHETERS

[75] Inventor: Benson F. Smith, Duluth, Ga.

[73] Assignee: C. R. Bard, Inc., Murray Hill, N.J.

[21] Appl. No.: 46,401

[22] Filed: Apr. 12, 1993

[51] Int. Cl.⁶ .................................................. A61M 31/00
[52] U.S. Cl. ...................................... 604/49; 128/772
[58] Field of Search ........................ 604/28, 49; 128/772, 128/656–658

[56] References Cited

U.S. PATENT DOCUMENTS

| | | | |
|---|---|---|---|
| 3,994,628 | 12/1976 | Gula et al. | 128/214.4 |
| 4,068,659 | 1/1978 | Moorehead | 128/214.4 |
| 4,091,922 | 5/1978 | Egler | 206/364 |
| 4,160,451 | 7/1979 | Chittenden | 128/214.4 |
| 4,205,675 | 6/1980 | Vaillancourt | 128/214.4 |
| 4,230,115 | 10/1980 | Walz, Jr. et al. | 128/295 |
| 4,243,033 | 1/1981 | DeCaprio et al. | 128/214.4 |
| 4,342,313 | 8/1982 | Chittenden | 128/214.4 |
| 4,379,506 | 4/1983 | Davidson | 206/364 |
| 4,397,091 | 8/1983 | Gustavsson et al. | 33/127 |
| 4,568,334 | 2/1986 | Lynn | 604/171 |
| 4,616,648 | 10/1986 | Simpson | 128/303 R |
| 4,652,256 | 3/1987 | Vaillancourt | 604/52 |
| 4,655,750 | 4/1987 | Vaillancourt | 604/165 |
| 4,713,059 | 12/1987 | Bickelhaupt et al. | 604/171 |
| 4,721,123 | 1/1988 | Cosentino et al. | 134/57 R |
| 4,737,145 | 4/1988 | Sharrow | 604/83 |
| 4,840,613 | 6/1989 | Balbierz | 604/51 |
| 4,844,092 | 7/1989 | Rydell et al. | 128/772 |
| 4,850,974 | 7/1989 | Bickelhaukpt et al. | 604/171 |
| 4,903,826 | 2/1990 | Pearce | 206/63.3 |
| 4,917,094 | 4/1990 | Lynch et al. | 128/657 |
| 4,932,413 | 6/1990 | Shockey et al. | 128/657 |
| 5,117,839 | 6/1992 | Dance | 128/772 |
| 5,125,902 | 6/1992 | Berry et al. | 604/164 |
| 5,125,905 | 6/1992 | Wright et al. | 604/171 |
| 5,125,906 | 6/1992 | Fleck | 604/158 |
| 5,125,914 | 6/1992 | Bassin | 604/275 |
| 5,135,535 | 8/1992 | Kramer | 606/194 |
| 5,247,942 | 9/1993 | Prather et al. | 128/657 |

FOREIGN PATENT DOCUMENTS

2215703  9/1989  United Kingdom ............ A61B 17/04

*Primary Examiner*—Jerome L. Kruter

[57] ABSTRACT

A method for withdrawing a first catheter inserted into a patient's vasculature over a resident guidewire, without removing the guidewire, is disclosed. The method includes the steps of providing an elongated tubular container having a proximal end and a distal end, and having an extension wire disposed therein for the length of the tubular container and axially secured to the proximal end of the container, axially connecting the distal end of the extension wire to the proximal end of the resident guidewire, and withdrawing the catheter over the resident guidewire and extension wire into the container. The method may further include steps of disconnecting the extension wire from the resident guidewire, providing a second elongated tubular container having a proximal end and a distal end, axially connecting the distal end of the second extension wire to the proximal end of the resident guidewire, and advancing the second catheter out of the second container over the second extension wire and the resident guidewire into the patient's vasculature.

8 Claims, 5 Drawing Sheets

METHOD OF WITHDRAWING AND EXCHANGING CATHETERS

FIELD OF THE INVENTION

This invention relates in general to a containment system for the handling of a catheter during a surgical procedure and, in particular, to an assembly that facilitates the removal and/or exchange of an in situ balloon catheter while maintaining a sterile environment for the balloon catheter and an extension guidewire.

BACKGROUND OF THE INVENTION

Guidewires are routinely used in medical procedures where a catheter is introduced into a patient's blood vessel such as an artery or vein. In cardiovascular procedures such as angioplasty, usually a guide catheter and a guidewire are inserted into the patient's blood vessel and advanced until the distal end of the guidewire reaches the location to be treated. Once the guidewire is in position, a catheter is slid over the guidewire and advanced until the catheter is positioned with its distal end at the diseased location within the patient.

During certain cardiovascular procedures, it may be desirable to change the in situ catheter. For example, a physician may use several balloon dilatation catheters having balloons of progressively increasing size to open a stenosis in the patient's artery. It is important to perform such a catheter exchange without moving the position of the guidewire from the location to be treated so that the guidewire can be used to direct the new catheter to the same location.

One often practiced method of exchanging catheters is to attach one end of an extension guidewire to the proximal end of the in situ guidewire and withdraw the catheter over the extension guidewire while leaving the in situ guidewire in place. A new catheter can then be advanced over the coupled guidewires, and the extension guidewire can be disconnected after the new catheter is placed at the location to be treated within the patient's vessel.

A disadvantage with this method is the difficulty in the physician's or nursing attendant's handling and manipulation of the extension guidewire and new catheter under the conditions in which cardiovascular procedures are performed. The length of extension guidewires has been typically in the order of 125 cm. This length of guidewire, which extends from the proximal end of the in sit guidewire, makes its handling somewhat awkward when the physician or attendant is attempting to exchange catheters in an already crowded operating room. At least one person must hold the extension guidewire with both hands to keep it and the catheter from contacting non-sterile objects or the floor, and, thus, breaching the sterile environment. Another person must manipulate the catheters around the first person's hands, keep the catheters from contacting the floor and other non-sterile objects, and avoid displacing the in situ guidewire all at the same time. As a result of these difficulties, the procedure of exchanging catheters is tedious, painstaking, time consuming and has some risk of displacement of the in situ guidewire.

Another disadvantage with this method of exchanging catheters is the problem of maintaining effective sterility, even if contact with non-sterile objects is avoided. Once the extension guidewire and the new catheter are removed from their sealed, sterile containers for use, there is no effective barrier to bacteria. Accordingly, there is some risk of infection by exposing the elongate guidewire and catheter to the open environment. As can be understood, all of these difficulties and complications add to the spiralling cost of medical procedures using guidewires and catheters.

Thus, there is a need for a device which can facilitate the procedure for handling and exchanging catheters, and which can provide for the sterile storage of a catheter therein.

In view of the foregoing, it is an object of the present invention to provide a device for facilitating catheter handling during an exchange of catheters in surgical procedures.

It is another object of the present invention to provide a device for the sterile storage of a catheter before, during, and after a catheter exchange.

It is yet another object of the present invention to provide a device for facilitating the exchange of catheters in a sterile environment that is simple in design and use, and economical to manufacture.

The foregoing objects and advantages of the invention are illustrative only and are not intended to be exhaustive or limiting of the possible advantages of the invention. These and other objects and advantages of the invention will be apparent from the description herein or from practicing the invention described or as modified to include any variations which may be apparent to those skilled in the art.

SUMMARY OF THE INVENTION

In accordance with the objects of the present invention, a brief summary of an exemplary embodiment is now presented. Some simplifications and omissions may be made in the following summary, which is intended to highlight and introduce some aspects of the present invention, but not to limit its scope. Detailed descriptions of an exemplary embodiment adequate to allow those of ordinary skill in the art to make and use the inventive concepts will be provided later.

According to a broad aspect of the invention, a catheter handling and storage system comprises a hollow tube for containing a balloon catheter having a bifurcated proximal end and including a guidewire leg and a non-guidewire leg. The tube has a proximal end and a distal end and preferably is configured as a loop or spiral. A securing means is located at the proximal end of the tube. An extension wire is coaxially disposed within the tube and secured to the proximal end of the tube by the securing means, with the extension wire extending longitudinally throughout the tube for guiding a catheter through the tube. The tube further includes a longitudinal slit extending from a proximal portion of the tube along the length of the tube to the distal end of the tube, for passing one end of the bifurcated proximal end of the catheter therethrough, to allow the catheter to be pulled over the extension wire and through the tube.

The subject invention is also directed to a method for handling a catheter. In accordance with the invention, the extension guidewire in the tube is axially connected to a guidewire that is resident in a patient and that extends out of the proximal end of an in situ catheter. The catheter is removed from the patient by sliding the catheter off of the resident guidewire and along the extension guidewire into the tube by passing the non-guidewire leg of the in situ catheter through the distal end of the slit in the tube to pull the catheter longitudinally through the tube. The guidewire leg of the catheter is slid along the extension guidewire in the tube as the catheter is pulled through the length of the tube. Thereafter, the catheter can be removed and a new catheter can be loaded into the catheter handling and storage system for advancement over the extension and in situ guidewires into the patient. Alternatively, a second catheter handling and storage system with a pre-loaded catheter can be used for connecting to the in situ guidewire after the first catheter is removed from the patient and stored in the first catheter handling and storage system.

It should be noted that the subject invention is not only directed to a method for exchanging catheters but is also directed to a method of simply withdrawing a catheter from a patient while maintaining the resident guidewire in the patient's vasculature.

The subject invention is also directed to a combination catheter assembly and catheter handling and storage system.

DETAILED DESCRIPTION OF PREFERRED EMBODIMENTS

The present invention contemplates a system for facilitating the handling and exchange of catheters during a surgical procedure.

Figure 1:
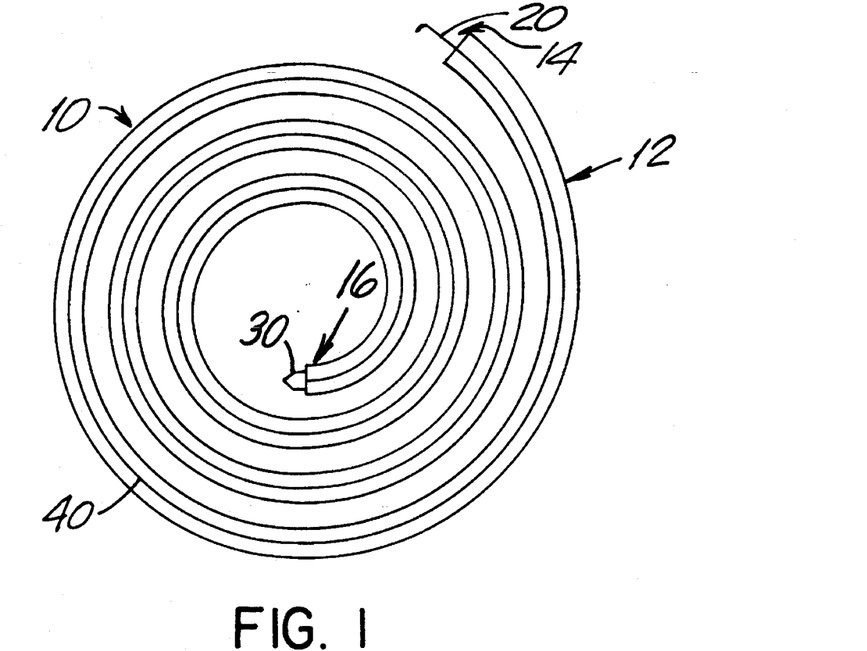
FIG. 1 is a top view of a catheter handling and storage system illustrating one embodiment of the present invention.
Figure 2:
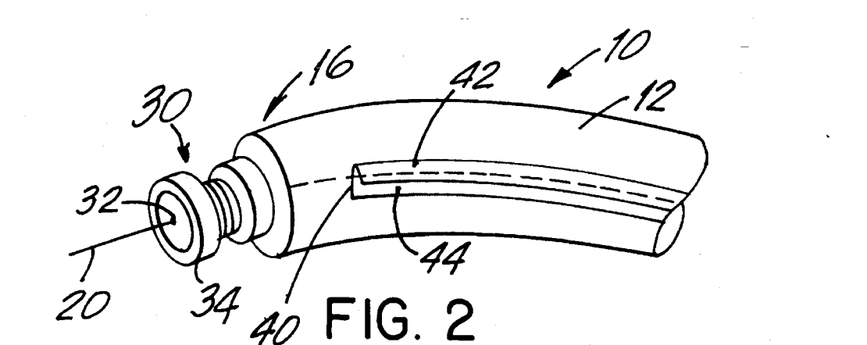
FIG. 2 is a perspective view of the proximal end of the catheter handling and storage system.
Figure 3:
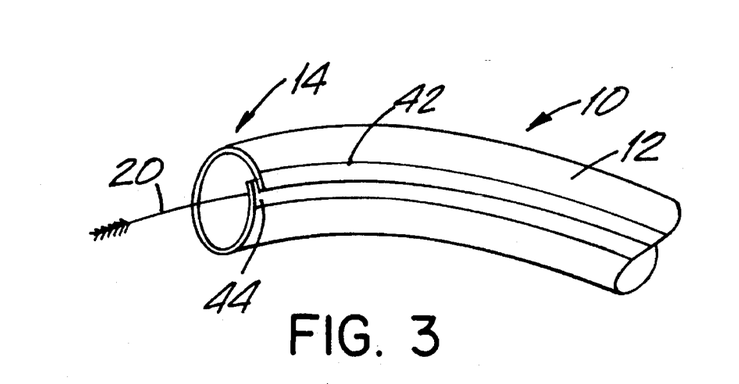
FIG. 3 is a perspective view of the distal end of the catheter handling and storage system.

Referring to FIGS. 1–3, there is illustrated one embodiment of the catheter exchange system (also referred to as a storage hoop) 10 according to the present invention.

The catheter exchange system 10 comprises a hollow tube which may be configured as a curve or spiral loop(s) (as shown in FIG. 1). According to the invention, the inner diameter of the tube 2 is such as to permit passage of a typical balloon catheter therein. An inner diameter of about 0.6 inches has been found to be workable, but the invention is not limited to such a diameter. The tube 12 is preferably constructed of a relatively rigid, yet resilient and smooth material such as a molded thermoplastic material. In choosing a suitable material, it is preferable that the tube 12 be made from a translucent or transparent plastic that allows some observation therein. However, the tube 12 may also be made of a metal, such as stainless steel. The tube 12 is open at its outer or distal end 14, and includes a clamp 30 at its inner or proximal end 16 to provide a means for securing or anchoring an extension guidewire 20 coaxially therein.

In the preferred embodiment, the clamp 30 may be a swivel clamp of a type similar to ones commercially available and known to those skilled in the art. The swivel clamp 30 may be dimensioned to fit within the inner diameter of tube 12, and may be secured therein through the use of an epoxy resin which, in addition to anchoring the clamp 30 to tube 12, effectively seals the proximal end of the tube. Notably, any suitable means such as an adhesive, bonding agent, mechanical snap-fit, or the like may be used to secure the swivel clamp 30 to the tube 12 and still be within the purview of the invention.

The following description of the swivel clamp 30, which is related to but does not in and of itself constitute the invention, is provided for illustrative purposes only. The swivel clamp 30 contains an anchor portion 36 that is fixed to the tube. An intermediate portion 37 is rotatably mounted onto the anchor portion and has an external thread 35 to which a cap 34 having an internal thread (not shown) is coupled. The cap 34 contains a centrally disposed through-channel or aperture 32 dimensioned to receive an extension guidewire 20 therethrough. The cap 34 and intermediate portion 37 cooperate such that variable gripping pressure can be applied to the extension guidewire 20 that is positioned within the sleeve-like aperture 32 as the cap 34 and intermediate portion 37 are screwed together. The cap 34 can be rotated so that sufficient pressure and frictional engagement can be applied to the extension guidewire 20 to secure it from movement relative to the tube 12. In this state, rotation of the cap and intermediate portion of the clamp effects rotation of the extension wire 20 within the tube. Such rotation of the extension wire 20 effects, as will be described below, the disconnection between the extension wire 20 and a guidewire residing in a patient. The cap 34 also may be unscrewed from intermediate portion 37 so that the extension guidewire 20 can be released for removal, advancement or exchange.

It should be noted that although the swivel clamp 30 (as described above) is preferred in the invention, it is not critical to the invention in that any suitable means for performing the functions described above, namely securing the guidewire 20 to the tube 12, may be used without departing from the scope of the invention.

In the preferred embodiment, the distal end 14 of the storage hoop 10 is simply an open end from which the extension guidewire 20 protrudes. It is, however, possible and perhaps desirable to provide the distal end 4 of the storage hoop with a coupling for attaching the storage hoop 10 to an in situ guiding catheter (not shown). The coupling may have many embodiments, but in its simplest form it may be a flexible sleeve dimensioned to fit inside or over the proximal end of the guiding catheter with an interference fit. It should be appreciated that the end of the storage hoop 10 can be configured in a variety of ways in order to be adaptable to various uses and for facilitation of the receiving of a variety of guiding catheters of different sizes and shapes.

As mentioned above, the extension guidewire 20 extends throughout the length of the tube 12 and is releasably secured to the swivel clamp 30. It is preferred that the extension guidewire 20 be of sufficient length to protrude past the distal end 14 of the tube 12 to enable easy connection to an in situ guidewire. The tube 12, in turn, is preferably longer than a typical balloon catheter (about 145 cm) so that any balloon catheter may be disposed within the tube 12 without its distal end protruding past the distal end 14 of the tube 12. Accordingly, the tube 12 may be preferably about 150 cm in length, and the extension guidewire 20 about 155 cm, but they are not so limited.

Figure 4:
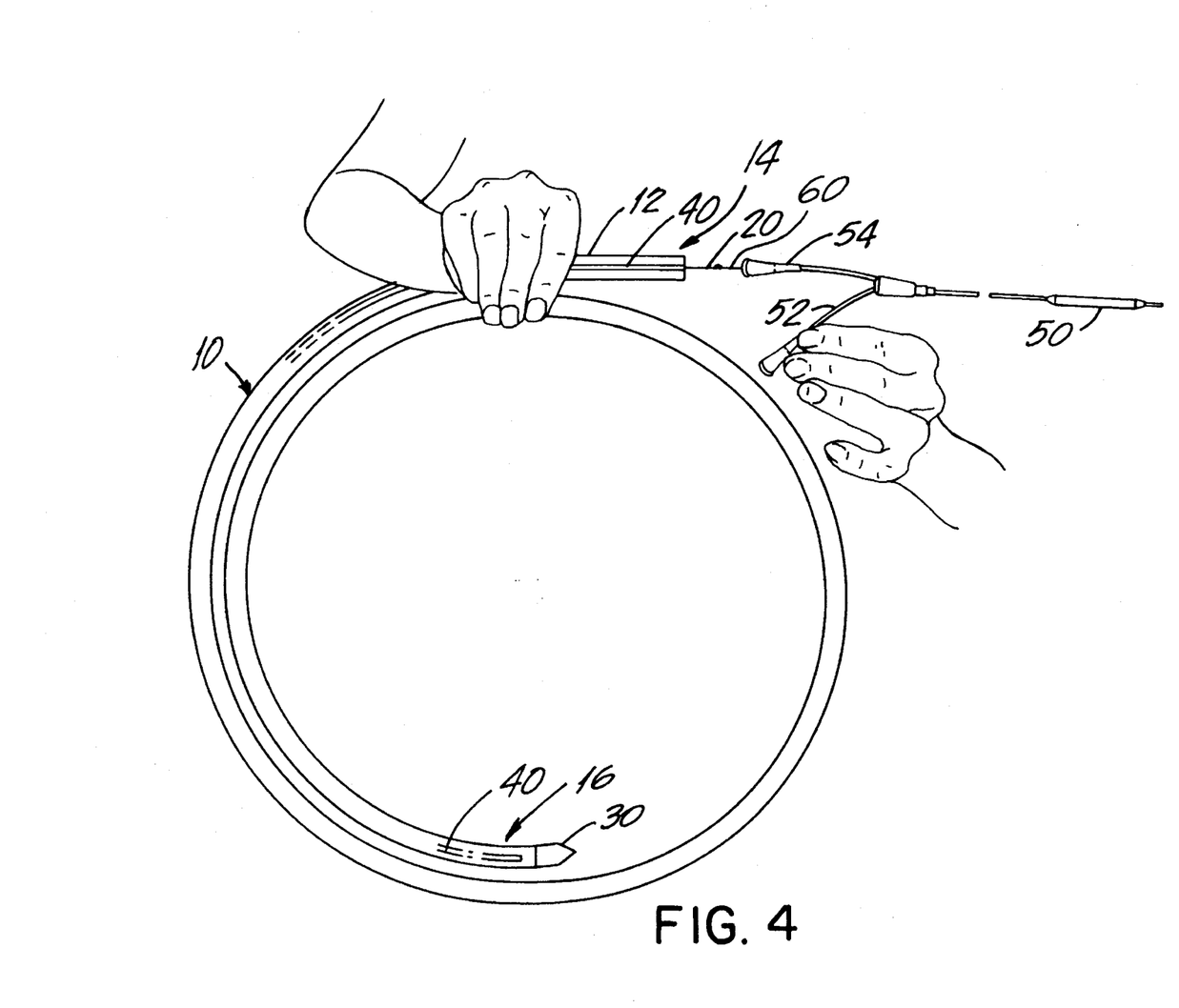
FIGS. 4–6 are elevational views illustrating the use of the catheter handling and storage system.

The tube 12 further includes a narrow, longitudinal slit 40 that begins at the distal end 14 of tube 12 and preferably extends to a portion just distal to the proximal end 16 of the tube (see FIG. 2). The distal end 14 of tube 12 defines a peripheral edge portion 21 (see FIG. 3). And slit 40 defines an opening 22 in edge portion 21. The slit 40 has a width so as to be able to pass the non-guidewire leg of a catheter having a bifurcated proximal end (as shown in FIG. 6)

therethrough with little tolerance. As shown in FIG. 4, catheter 50 includes a bifurcated proximal end comprising a guidewire leg 54 having a catheter proximal wire port 55 through which guidewire 60 passes, and non-guidewire leg 52. A distal wire port 56 is provided at the distal end of the catheter. Accordingly, the slit 40 may have a width of about 0.090 inches, but it is not so limited. Preferably, slit 40 flares at opening 22 to facilitate passage of non-guidewire leg 52 into slit 4 (see FIG. 6). In its preferred embodiment, the slit 40 includes flaps 42 and 44 which are dimensioned so that the edge of one flap 42 rests over the edge of the other flap 44, so as to close the slit. See FIGS. 2 and 3. Both flaps 42 and 44 may be made from a thin-wall plastic material, such as polyethylene, that is sufficiently flexible to allow the non-guidewire leg of a catheter to pass through the slit with a close fit such that the flaps 42, 44 spread apart only in the areas adjacent to the protruding catheter leg. Advantageously, the flaps 42, 44 are continuously urged into a closed, sterile disposition to prevent unnecessary contamination of the catheter and extension guidewire 20 disposed within the storage hoop 10.

Figure 5:
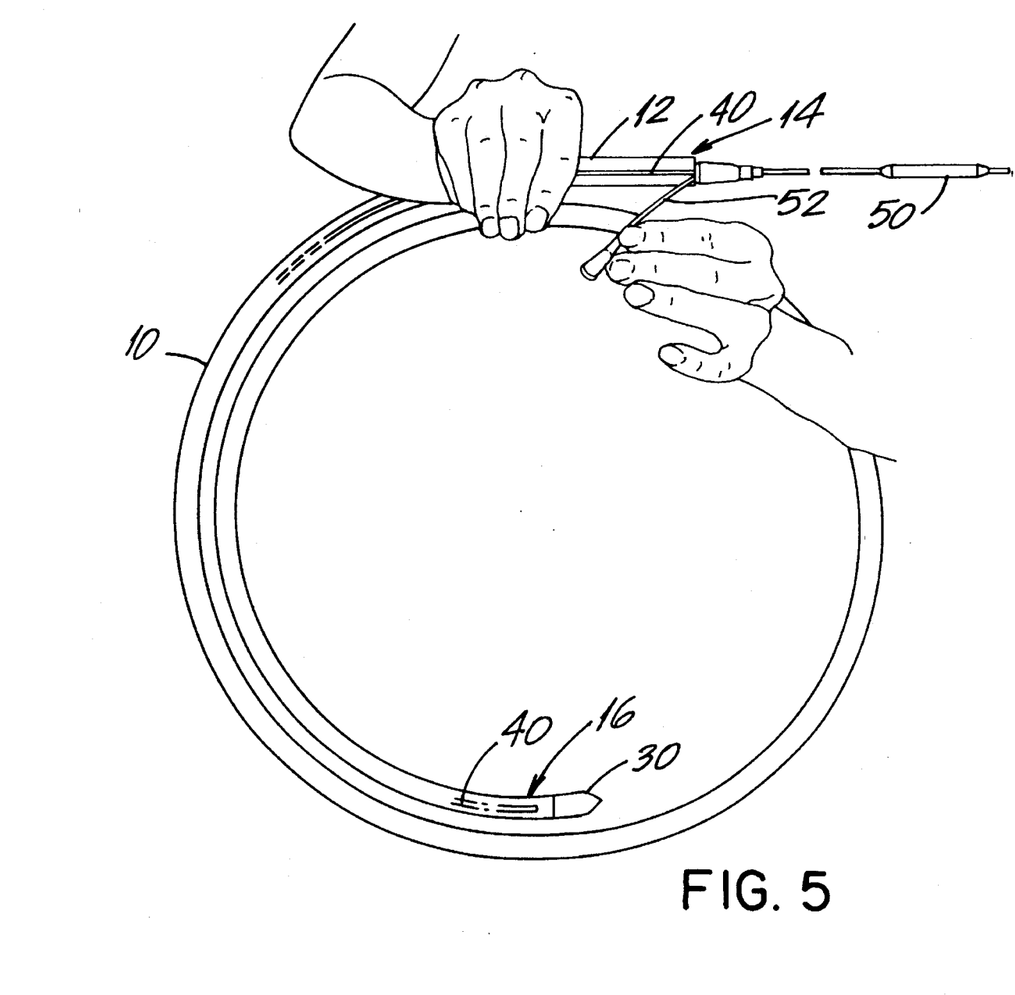
Figure 6:
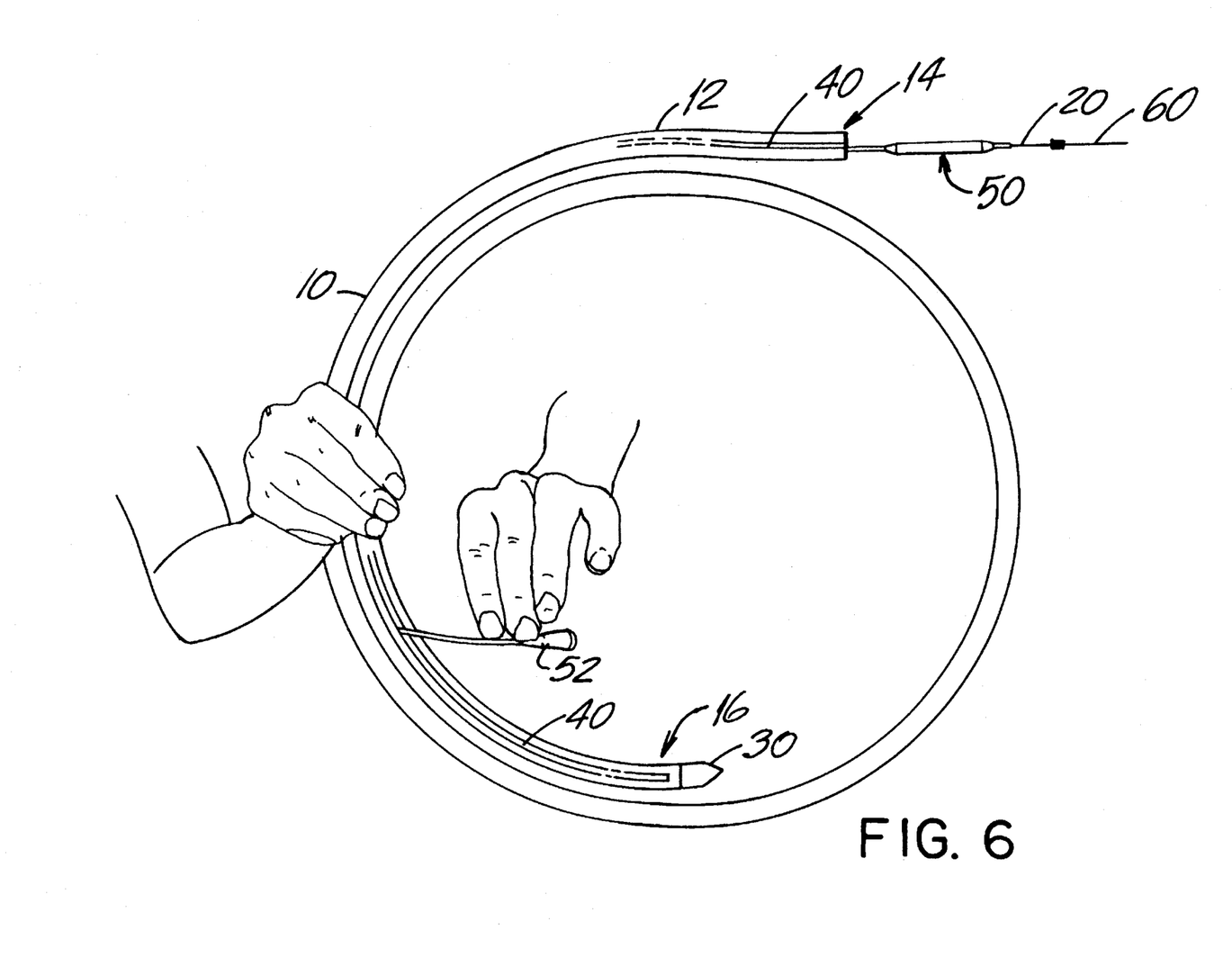

By way of example and with reference to FIGS. 4–6, when it is desired to remove a balloon catheter 50 that is resident in a patient, the storage hoop 10 having a pre-installed and secured extension guidewire 20 is aligned with the guidewire 60 that is resident in the patient and that extends out of the proximal end of the in situ catheter 50. The extension guidewire 20 of the storage hoop 10 is then attached in-line to the resident guidewire 60 using conventional practices known to those skilled in the art. For instance, see U.S. Pat. No. 5,133,364. The catheter 50 may be removed from the patient by sliding the catheter 50 along the resident guidewire 60 and then along the extension guidewire 20 into the storage hoop 10.

To accomplish this, non-guidewire leg 52 of the resident catheter 50 is passed through the distal end of the slit 40, between flaps 42 and 44, as the catheter 50 is pulled from the patient's body and drawn into the storage hoop. The catheter 50 may be pulled through the storage hoop 10 by the non-guidewire leg 52 which slides along slit 40 while guidewire leg 54 of the catheter 50 is slid along the extension guidewire 20 in the storage hoop 10. The closed slit 40, which runs lengthwise of the tube, facilitates the pulling of the catheter 50 through the tube 12 while preventing the catheter from "falling out" of the tube 12.

Once the proximal end of the catheter 50 is slid along the extension guidewire 20 to the proximal or inner end 16 of the storage hoop 10, the extension guidewire 20 may be disconnected from the resident guidewire 60. This may be done, for example, by rotating swivel clamp 30 counterclockwise to cause extension wire 20 to also rotate so as to separate it from resident guidewire 60, as in the case where the extension wire and the resident guidewire are attached as described in U.S. Pat. No. 5,133,364. The used catheter 50 may now be removed from the storage hoop 10 by pulling the distal end of the catheter out of the tube and off extension wire 20.

In practice, a physician may use one storage hoop 10 for the whole procedure by replacing the catheter 50 that was slid into the storage hoop 10, with a new catheter, which may be later introduced into the body of the patient. This may be done by inserting the distal end of extension guidewire 20 into the guidewire leg of the new catheter and pulling the catheter through tube 12 and along the extension wire 20 as described above until the distal end of extension wire 20 protrudes from the distal wire port of the catheter. The extension guidewire 20 and the resident guidewire 60 may then be reattached and the catheter pulled out of the distal end of tube 12 and slid along guidewire 60 into the patient.

Alternatively, the physician may use a second storage hoop 10 pre-loaded with the new catheter and extension wire 20 that can be connected to the resident guidewire 60 after the first catheter 50 is removed from the patient's body and placed in the first storage hoop 10 and the resident guidewire 60 disconnected from the old extension wire.

Figure 7:
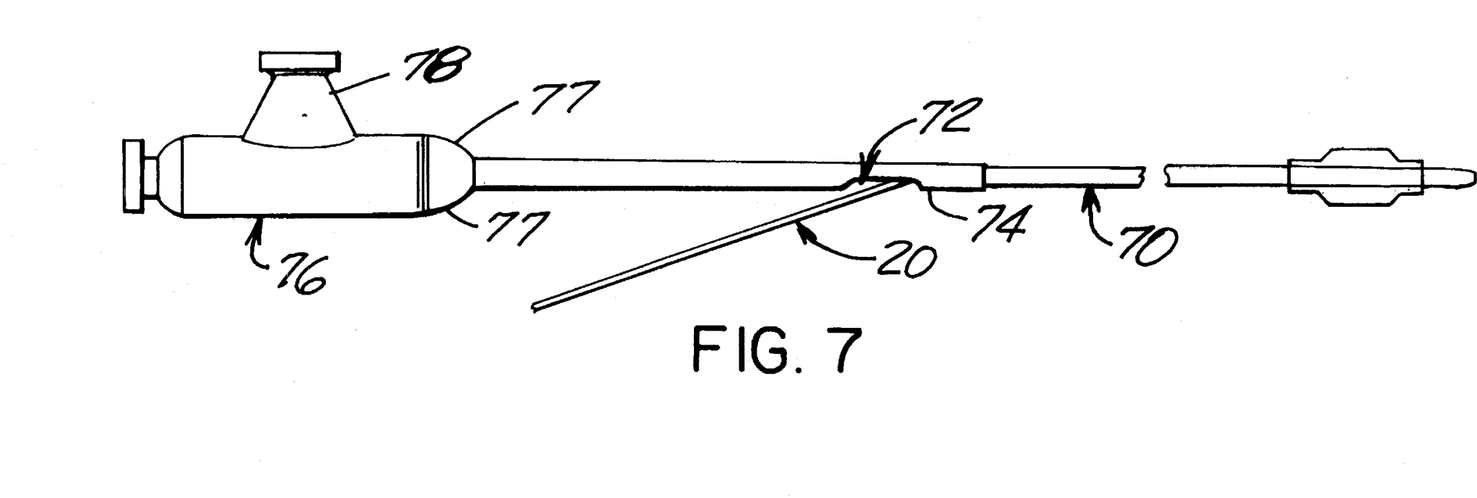
FIG. 7 is an elevational view of an embodiment of a catheter designed specifically for the catheter handling and storage system.

Notably, the storage hoop 10 works with both conventional balloon catheters and with catheters designed specifically for the storage hoop 10. In FIG. 7, a catheter 70 designed specifically for use with the storage hoop is shown. As illustrated, catheter 70 may be one which does not include a bifurcated proximal end having a guidewire leg with a luer fitting (as shown in FIG. 4). Instead, the catheter 70 may be similar to so-called "monorail" type catheters that are known to those skilled in the art. Accordingly, as shown in FIG. 7, the catheter 70 includes a small aperture or skive 72 near the proximal end of the catheter shaft 74 which defines a proximal wire port for receiving the guidewires 20 or 60.

As in the case when a bifurcated catheter is used with the storage hoop 10, the catheter 70 is guided over the extension guidewire 20 (which enters the catheter 70 through port 72) into the tube 12 while pulling the catheter 70 by its proximal end. Similar to the procedure described above, the proximal end of the catheter passes through the slit 40 and lies exterior to tube 12 as the portion of catheter 70 distal to port 72 is pulled through the tube 12.

With this arrangement, the tube 12 can be made with a small diameter, only slightly larger than the diameter of the catheter shaft 74, because no fittings will be present inside of the tube 12. The only fitting on this catheter 70 remains outside at the tube 12. A small diameter is advantageous for the tube 12 to reduce bulk, weight, etc., making the storage hoop 10 easier to handle, while at the same time reducing medical plastic disposal volume, etc.

Figure 8:
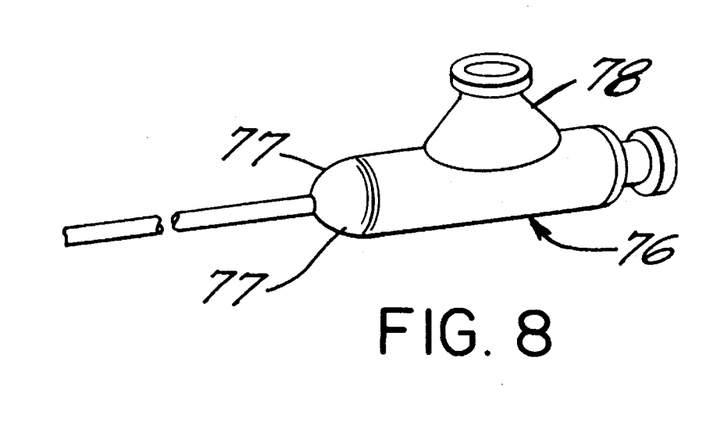
FIG. 8 is an isometric view of an embodiment of the proximal end of another catheter designed specifically for the catheter handling and storage system.

Turning now to FIG. 8, there is illustrated another embodiment of a catheter that may be used with the subject storage hoop. In this embodiment, the bifurcated assembly 76 preferably has a sleeker shape including radiused edges 77 (e.g., like that of a submarine) to facilitate its passage through the storage hoop 10.

In this embodiment, the bifurcated assembly 76 includes a guidewire receiving portion 79 and an inflation or non-guidewire portion 78 that protrudes from the guidewire portion. Preferably, guidewire portion 79 is sleeker in profile than the corresponding portion of conventional catheters and includes radiused edges 77 to facilitate the passage of guidewire portion 79 through the storage hoop. In addition, the body 80 of inflation portion 78 is preferably generally elliptical in cross-section, as opposed to circular, so as to have a thin, fin-like shape. The fitting 81 for attaching the catheter to a source of inflation fluid may be circular as it does not have to pass through the slit of the storage hoop. It is contemplated that the catheter of FIG. 8 be used with a storage hoop 10 whose slit 40 is smaller than the thickness of the inflation portion 72 or which includes overlapping flaps 42 and 44. Thus, when the catheter 70 is slid through the storage hoop 10, the inflation portion 78 spreads apart the slit 40 or the flaps 42 and 44 only in the areas adjacent to the inflation portion 78. This permits a more sterile storage of any catheter disposed therein since the storage hoop 10 is closed in all places along its length except for the area in which the inflation portion 78 is protruding therethrough. Thus, the storage hoop 10 of the present invention not only facilitates the handling of catheters, but also provides for a sterile enclosure to reduce the risk of exposing such catheters to bacteria in the environment.

It is to be understood that the present invention may be used with equal facility and advantage in a wide variety of catheter devices, both dilatation and non-dilatation. Moreover, although the invention has been described in detail with particular reference to preferred embodiments thereof, it should be understood that the invention includes other and different embodiments. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A method for handling a catheter inserted into a desired position in a patient's vasculature over a resident guidewire without removing the resident guidewire, said resident guidewire having a proximal end and a distal end, the proximal end of said resident guidewire being disposed exterior to the patient's vasculature, the method comprising the steps of:

providing an elongate tubular member having a proximal end and a distal end, said tubular member having an extension wire secured to the proximal end of said tubular member and extending through said tubular member and out the distal end of said tubular member, said tubular member further including a longitudinal slit extending from a proximal portion of the tubular member to the distal end of said tubular member;

axially connecting the distal end of said extension wire to the proximal end of the resident guidewire;

withdrawing said catheter from the patient's vasculature over said resident guidewire and said extension wire, said catheter having a wire lumen for receiving said resident guidewire and said extension wire, said catheter further including a proximal wire port and a distal wire port, each of said ports being in communication with said wire lumen;

inserting a first portion of said catheter into the distal end of said tubular member;

passing a second portion of said catheter into the distal end of said tubular member and through the slit such that said second catheter portion protrudes exteriorally from said tubular member through said slit; and sliding said catheter proximally through said tubular member along the extension wire by sliding the second portion of the catheter proximally along said slit until the distal end of said extension wire extends out of the distal wire port of said catheter.

2. The method of claim 1 which further includes the steps of:

disconnecting the extension wire from said resident guidewire; and removing said catheter from said tubular member and extension wire by sliding said catheter second portion distally along said slit to slide the catheter distally along the extension guidewire and through said tubular member until the distal end of the extension wire exits the proximal wire port of the catheter.

3. The method of claim 2 which further comprises the steps of:

providing a second catheter having a wire lumen for receiving said extension wire and said resident guidewire, said lumen extending from a proximal wire port to a distal wire port;

inserting the distal end of said extension wire into the proximal wire port and wire lumen of said second catheter;

inserting a first portion of said second catheter into the distal end of said tubular member;

passing a second portion of said second catheter into the distal end of said tubular member and through said slit such that said second portion of said second catheter protrudes exteriorally of said tubular member through said slit; and sliding said second catheter proximally through said tubular member along the extension wire therein by sliding the second portion of the second catheter proximally along the slit until the distal end of the extension guidewire protrudes from the distal wire port of said second catheter.

4. The method of claim 3 which further comprises the steps of:

axially connecting the distal end of the extension wire to the proximal end of the resident guidewire to form a wire joint portion;

sliding said second catheter distally through said tubular member along said extension wire by sliding the second catheter portion of said second catheter distally along said slit;

passing the second portion of said second catheter out of the distal end of said tubular member;

inserting the wire joint portion into the proximal wire port of said second catheter; and advancing said second catheter along said resident guidewire to the desired position in the patient's vasculature.

5. The method of claim 1 which further includes the steps of:

disconnecting the extension wire from said resident guidewire;

providing a second elongated tubular member having a proximal end and a distal end, said second tubular member having a second extension wire secured to the proximal end of said second tubular member and extending through said second tubular member and out the distal end of said second tubular member, said second tubular member further including a longitudinal slit extending from a proximal portion of the second tubular member to the distal end of said second tubular member, said second tubular member further including a second catheter member having a first portion disposed within the second tubular member, said first portion including a wire lumen and a proximal wire port and a distal wire port, each of said proximal and distal wire ports communicating with the wire lumen of said second catheter, said second elongated wire member being disposed within said wire lumen of the second catheter and extending out the distal wire port of the second catheter, said second catheter having a second portion extending through the longitudinal slit so as to protrude exteriorally from the second tubular member;

axially connecting the distal end of the second extension wire to the proximal end of the resident guidewire to form a wire joint portion;

sliding said second catheter distally through said second tubular member along said second extension wire by sliding the second catheter portion of said second catheter distally along the slit of said second tubular member;

passing the second portion of said second catheter out the distal end of said second tubular member;

inserting the wire joint portion into the proximal wire port of said second catheter; and advancing said second catheter along said resident guidewire to the desired position in the patient's vasculature.

6. A method for withdrawing a first catheter inserted into a patient's vasculature over a resident guidewire without removing the resident guidewire, the resident guidewire having a proximal end and a distal end, comprising the steps of:

providing an elongated tubular container having a proximal end and a distal end, and having an extension wire disposed therein for the length of the tubular container and axially secured to the proximal end of said container, said extension wire having a distal end:

withdrawing aid catheter over said resident guidewire and said extension wire into said container:

disconnecting the extension wire from the resident guidewire;

removing said first catheter from said container;

inserting a second catheter into said container over said extension wire;

axially connecting the distal end of the extension wire to the proximal end of the resident guidewire; and advancing said second catheter over said coaxial extension wire and the resident guidewire into the patient's vasculature.

7. A method for withdrawing a first catheter inserted into a patient's vasculature over a resident guidewire without removing the resident guidewire, the resident guidewire having a proximal end and a distal end, comprising the steps of:

providing an elongated tubular container having a proximal end and a distal end, and having an extension wire disposed therein for the length of the tubular container and axially secured to the proximal end of said container, said extension wire having a distal end;

axially connecting the distal end of said extension wire to the proximal end of the resident guidewire:

withdrawing said catheter over said resident guidewire and said extension wire into said container:

disconnecting the extension wire from the resident guidewire;

providing a second elongated tubular container having a proximal end and a distal end, said second container including a second catheter disposed within said second container and a second extension guidewire secured to the proximal end of said second container and being slidably disposed within a wire lumen in said second catheter, said second extension wire having a proximal end and a distal end;

axially connecting the distal end of said second extension wire to the proximal end of the resident guidewire; and advancing said second catheter out of said second container over said second extension wire and the resident guidewire into the patient's vasculature.

8. The method according to claim 7, wherein said elongated tubular containers each has a generally coiled configuration to facilitate handling thereof.

* * * * *

UNITED STATES PATENT AND TRADEMARK OFFICE
CERTIFICATE OF CORRECTION

PATENT NO. : 5,454,785
DATED      : October 3, 1995
INVENTOR(S) : Benson F. Smith It is certified that error appears in the above-indentified patent and that said Letters Patent is hereby corrected as shown below:

In col. 9, line 23, "aid catheter" should read -- said catheter--.

Signed and Sealed this

Thirteenth Day of February, 1996

Attest:

BRUCE LEHMAN

*Attesting Officer*    *Commissioner of Patents and Trademarks*